(12) United States Patent
Ochs et al.

(10) Patent No.: US 7,848,805 B2
(45) Date of Patent: Dec. 7, 2010

(54) MODULAR MEDICAL DEVICE, BASE UNIT AND MODULE THEREOF, AND AUTOMATED EXTERNAL DEFIBRILLATOR (AED), METHODS FOR ASSEMBLING AND USING THE AED

(75) Inventors: Dennis E. Ochs, Bellevue, WA (US); Robert T. Shen, Kirkland, WA (US); Daniel J. Powers, Issaquah, WA (US); Anthony G. Picardo, Tacoma, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 130 days.

(21) Appl. No.: 12/105,615

(22) Filed: Apr. 18, 2008

(65) Prior Publication Data

US 2009/0125074 A1    May 14, 2009

Related U.S. Application Data

(63) Continuation-in-part of application No. 10/844,005, filed on May 11, 2004, now abandoned, which is a continuation of application No. 09/909,605, filed on Jul. 20, 2001, now abandoned.

(51) Int. Cl.
*A61N 1/00* (2006.01)
(52) U.S. Cl. .......................................................... 607/5
(58) Field of Classification Search .................. 307/85; 312/213; 324/434; 370/338; 600/300, 509; 607/5, 30, 32, 60
See application file for complete search history.

(56) References Cited

U.S. PATENT DOCUMENTS

| 3,865,101 | A |   | 2/1975  | Saper et al. |       |
|-----------|---|---|---------|--------------|-------|
| 4,895,161 | A |   | 1/1990  | Cudahy et al.|       |
| 5,607,454 | A |   | 3/1997  | Cameron et al.|      |
| 5,611,815 | A |   | 3/1997  | Cole et al.  |       |
| 5,662,690 | A |   | 9/1997  | Cole et al.  |       |
| 5,697,958 | A | * | 12/1997 | Paul et al.  | 607/31|
| 5,713,927 | A |   | 2/1998  | Hompele et al.|      |
| 5,716,380 | A | * | 2/1998  | Yerkovich et al.| 607/5 |
| 5,735,879 | A |   | 4/1998  | Gliner et al.|       |

(Continued)

FOREIGN PATENT DOCUMENTS

DE        19751024 A      5/1999

(Continued)

*Primary Examiner*—George Manuel
*Assistant Examiner*—Robert N Wieland
(74) *Attorney, Agent, or Firm*—W. Brinton Yorks, Jr.

(57) ABSTRACT

A modular automated external defibrillator (AED) system includes a base unit and at least one interconnected module. The base unit typically includes a functional circuit and includes an interface that couples the functional circuit to the module. Likewise, the module includes an interface that couples the module to the base unit. By manufacturing such modular AED models instead of one-piece, i.e., integrated, AED models, a manufacturer can reduce the cost and complexity of its manufacturing process. Furthermore, the manufacturer may be able to bring such a modular AED to market more quickly than it could bring an integrated model of the AED to market. Moreover, a modular AED allows the manufacturer and customer flexibility in respectively providing and selecting feature sets. In addition, a customer can obtain replacements for broken modules, and the manufacturer can provide cheaper upgrades by upgrading a module or base unit instead of upgrading the entire AED.

7 Claims, 13 Drawing Sheets

U.S. PATENT DOCUMENTS

| | | |
|---|---|---|
| 5,836,993 A | 11/1998 | Cole |
| 5,879,374 A | 3/1999 | Powers et al. |
| 5,993,219 A | 11/1999 | Bishay |
| 6,088,617 A | 7/2000 | Arand et al. |
| 6,128,530 A | 10/2000 | Galen et al. |
| 6,269,266 B1 * | 7/2001 | Leysieffer .................. 607/2 |
| 6,422,669 B1 * | 7/2002 | Salvatori et al. ............ 312/213 |
| 6,438,417 B1 | 8/2002 | Rockwell et al. |
| 6,577,901 B2 * | 6/2003 | Thompson .................. 607/60 |
| 6,591,135 B2 | 7/2003 | Palmer et al. |
| 6,659,947 B1 * | 12/2003 | Carter et al. ............... 600/300 |
| 6,693,431 B1 * | 2/2004 | Leyde et al. ................ 324/434 |
| 2002/0082644 A1 | 6/2002 | Picardo et al. |
| 2002/0165458 A1 * | 11/2002 | Carter et al. ............... 600/509 |
| 2004/0170154 A1 * | 9/2004 | Carter et al. ............... 370/338 |
| 2006/0287694 A1 * | 12/2006 | Almendinger et al. ........ 607/60 |

FOREIGN PATENT DOCUMENTS

| | | |
|---|---|---|
| EP | 0757912 A2 | 2/1997 |
| EP | 1002555 A2 | 5/2000 |
| WO | 9847409 | 10/1998 |
| WO | 0166182 | 9/2001 |

\* cited by examiner

MODULAR MEDICAL DEVICE, BASE UNIT AND MODULE THEREOF, AND AUTOMATED EXTERNAL DEFIBRILLATOR (AED), METHODS FOR ASSEMBLING AND USING THE AED

This application is a continuation in part of U.S. patent application Ser. No. 10/844,005, filed May 11, 2004 now abandoned which is a continuation of U.S. patent application Ser. No. 09/909,605, filed Jul. 20, 2001 and now abandoned.

The invention relates generally to medical devices, and more particularly to a modular automated external defibrillator (AED), the base unit and modules of the AED, and methods for assembling and using the AED. The modular AED may be manufactured less expensively than a comparable non-modular, i.e., integrated, AED. Furthermore, being a modular AED may facilitate the FDA (Food and Drug Administration) approval/clearance process of the base unit and subsequent combinations of the base unit and modules.

AEDs, which have saved many lives in non-hospital settings, are becoming easier to use; consequently, the demand for AEDs is rising. Typically, an AED analyzes a patient's heart rhythm and, if appropriate, instructs an operator to administer an electrical shock to the patient. For example, a shock can often revive a patient who is experiencing ventricular fibrillation (VF). Because many models of AEDs include only basic diagnostic and safety features, they are often difficult to operate. Therefore, only specially trained persons such as emergency medical technicians (EMTs) can use these older models to administer shocks to patients. Newer models, however, often include advanced diagnostic and safety features that allow minimally trained persons to administer shocks to patients. Consequently, more businesses and individuals are acquiring AEDs to save lives.

A variety of AED models are currently available. For example, some models allow an operator to make few if any decisions regarding treatment of a patient, and thus are suitable for untrained or minimally trained operators. Conversely, other models allow an operator great flexibility in directing the patient's treatment, and thus are suitable for trained operators such as EMTs. Furthermore, some models provide audible or readable instructions in respective languages, typically one language per model. In addition, some models are lower-priced because they include a basic set of features, and other models are higher priced because they include a more comprehensive set of features.

Referring to FIG. 1, most AED models are manufactured, tested, FDA approved, and sold as one-piece, i.e., integrated, units.

FIG. 1 illustrates a conventional AED system 10, which includes an integrated AED 12 having a one-piece, i.e., integral, housing 14, and which includes defibrillator electrode pads 16a and 16b. The AED 12 includes a battery 18 for supplying power, an on/off key switch 20, a display 22 for displaying readable operator instructions, cardiac waveforms, or other information, a speaker 24 for providing audible operator instructions, an AED status indicator 26, a contrast control 27 for the display 22, and a shock button 28, which the operator (hands shown in FIG. 1) presses to deliver a shock to a patient (not shown). The AED 12 also includes a connector 30, which receives a pad connector 32 to allow coupling of the pads 16a and 16b to the AED. Furthermore, the AED 12 may include a microphone 34 for recording the operator's voice and other audible sounds that occur during the rescue, and a storage device such as a data card 36 for storing these sounds along with the patient's ECG and a record of AED events for later study. And in addition to being able to defibrillate the patient, the AED 12 may be able to pace, cardiovert, or provide other electrotherapy to the patient, or may have a manual override that allows the operator more control over otherwise automated functions.

Because it is an integrated unit, introducing a modified version of the AED 12 to respond to specific customer requirements typically requires a manufacturer to design and produce a separate model of the AED. Removing the contrast control 27, changing the language of the audible or displayed operator instructions, removing the status indicator 26, and changing the shape of the housing 12 are examples of modifications that typically require the manufacturer to produce a separate AED model. Moreover, different customers may want the AED 12 to be capable of different electrotherapies or combinations of electrotherapies. For example, one customer may want the AED 12 to be capable of defibrillation only, and another customer may want the AED to be capable of pacing, cardioversion, and defibrillation. Consequently, the manufacturer would typically have to produce a separate AED model for each supported electrotherapy or combination of electrotherapies.

Unfortunately, the more models of integrated AEDs a manufacturer produces, the more complex and expensive its overall manufacturing and logistical operations. An AED model may be manufactured independently of other AED models. That is, a model may have its own dedicated assembly/test line, and thus may have its own dedicated manufacturing/testing equipment, assemblers, testers, and troubleshooters. If the model is discontinued, then the equipment may be useless to the manufacturer, or may need revamping for use with other models. Also, the manufacturer may need to retrain the assemblers, testers, and troubleshooters for another model. Furthermore, because materials and components are typically more expensive if purchased in smaller lots, producing different AED models having different materials or components may increase the manufacturer's costs for materials and components. Moreover, the manufacture often must receive FDA approval of each model. The FDA-approval process takes time and may lengthen a model's time to market. These problems may also plague manufacturers of integrated medical devices other than AEDs.

Consequently, there is a need for a medical device, such as an AED, that avoids some or all of the shortcomings of a conventionally integrated medical device.

A modular AED includes an interconnected base unit and one or more modules. A base unit includes a functional base-unit circuit and a base-unit interface that electronically couples the circuit to a module. And the module includes a module interface that electronically couples the module to the base unit. Such a modular AED is often easier and less expensive to manufacture than an integrated AED. For example, if multiple models of a modular AED incorporate the same base unit and some of the same modules, then the manufacturer can often purchase common components in larger lots and reduce the number of assembly/testing lines as compared to several integrated devices. Furthermore, the manufacturer may reduce the overall time required for FDA approval by seeking separate approval for different base units and modules. For example, if the manufacturer introduces a new model having an approved base unit but one or more new, unapproved modules, then the manufacturer may need FDA approval of the new modules only. The approval process for the new modules may be easier, faster, and cheaper than an approval process for a comparable integrated model or for the whole new model, i.e., the intercoupled base unit and new modules.

The following discussion is presented to enable a person skilled in the art to make and use the invention. As used herein, the term "automated external defibrillator" or "AED" is any defibrillator that determines whether a patient has a shockable heart rhythm.

Figure 1:
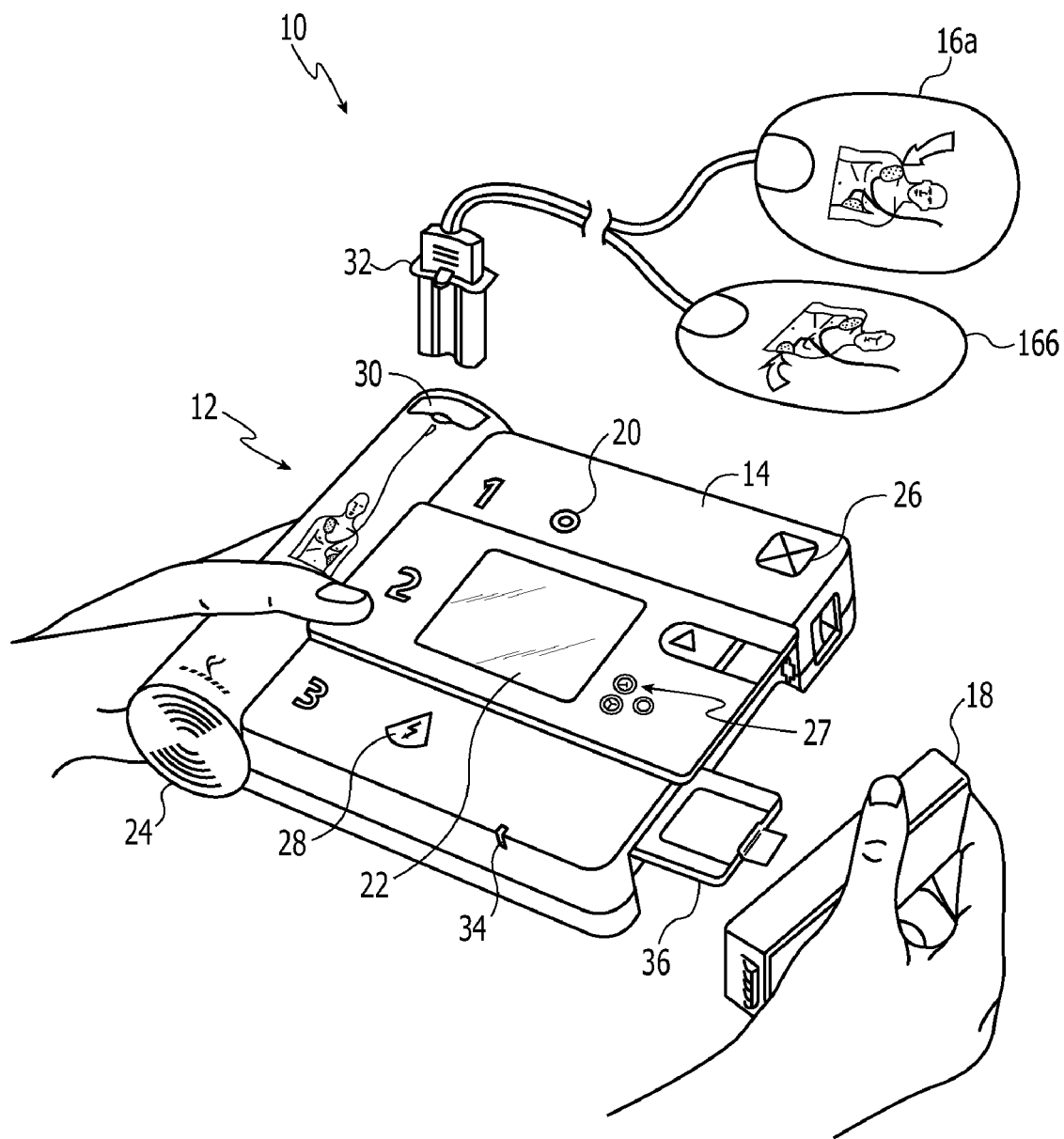
FIG. 1 is a view of a conventional AED system that includes an integrated AED.
Figure 2:
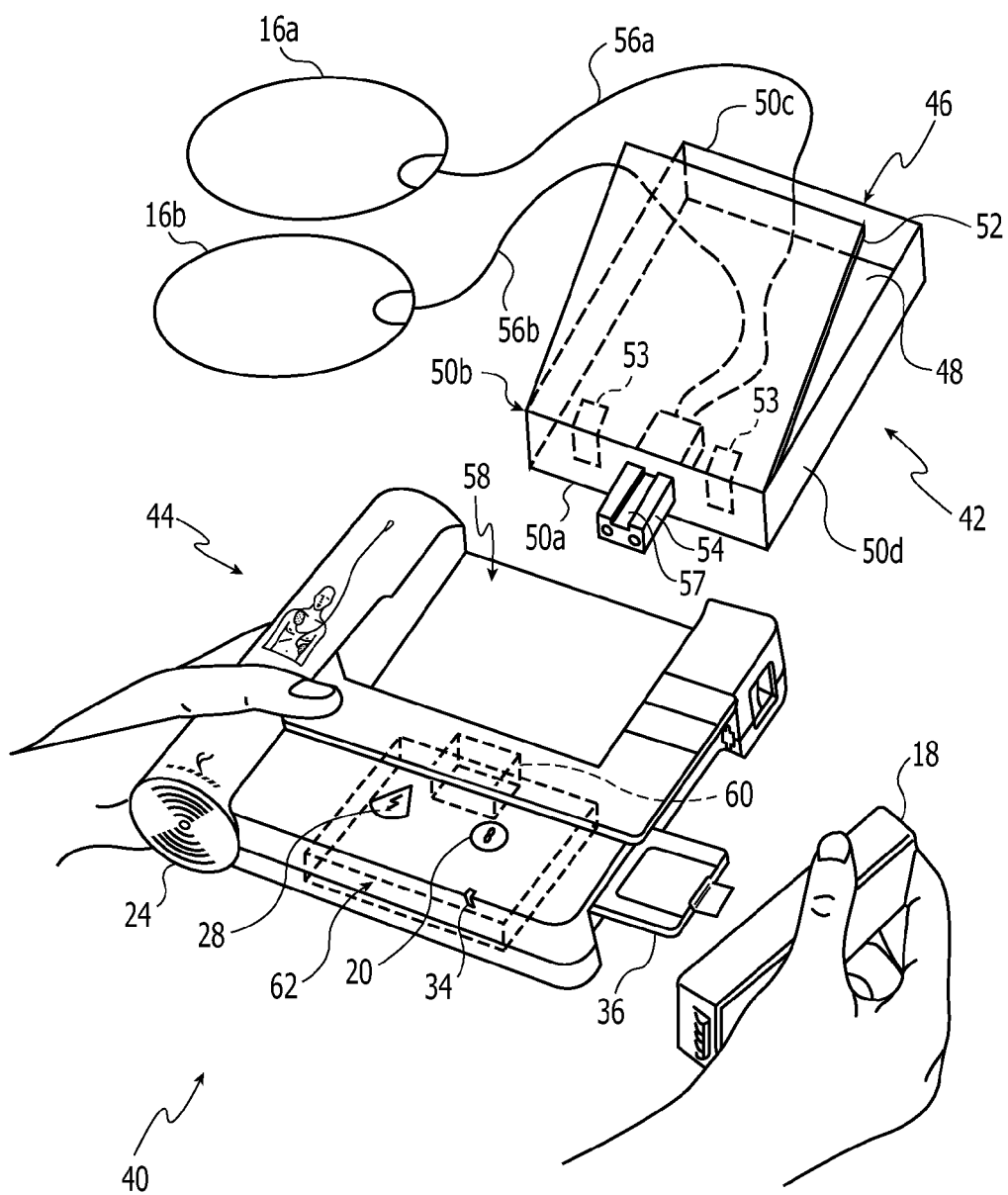
FIG. 2 is an exploded view of a modular AED according to an embodiment of the invention.

FIG. 2 is an exploded view of a modular AED system 40, which includes a pad-cartridge module, i.e., cartridge assembly, 42 and an AED base unit 44 according to an embodiment of the invention. For clarity, like numerals refer to elements common to the system 10 of FIG. 1. The modular AED system 40 is often easier and less expensive to manufacture than the integrated AED system 10 of FIG. 1. For example, multiple models of the modular AED system 40 may incorporate the same base unit 44. Therefore, the manufacturer can often purchase components for the base unit 44 in relatively large lots, and have a single assembly/testing line for the base unit. Furthermore, once the FDA has approved the base unit 44, the manufacturer typically need only obtain FDA approval for new modules to be incorporated into the AED system 40. Similarly, once the FDA has approved a module, the manufacturer typically need only obtain FDA approval for new base units to be incorporated into the AED system 40.

The cartridge assembly 42 includes the electrode pads 16a and 16b and a cartridge 46. The cartridge 46 has a bottom, i.e., tray, 48, side walls 50a-50d, and lid 52, which may be hinged to a side wall such as the side wall 50a with one or more hinges 53. The cartridge 46 also includes an electrode-pad connector 54, which may extend through a side wall such as the side wall 50a, helps to secure the cartridge 46 to the AED base unit 44, and electrically connects the electrode pads 16a and 16b to the base unit via electrode-pad wire leads 56a and 56b. Alternatively, the connector 54 may extend through the tray 48. The leads 56a and 56b are conventionally attached to the connector 54. The connector 54 may include an information provider such as a groove 57, which provides information, such as the type (e.g., pediatric, adult, or training) of pads 16a and 16b, to the base unit 44. The cartridge 46 may also include a conventional latch mechanism (not shown) for latching the lid 52 to one or more of the side walls 50a-50d. This and other embodiments of the cartridge assembly 42 are further discussed in U.S. patent application Ser. No. 09/746,123, entitled CARTRIDGE FOR STORING AN ELECTRODE PAD AND METHODS FOR USING AND MAKING THE CARTRIDGE, filed on Dec. 22, 2000, which is incorporated by reference.

Still referring to FIG. 2, in addition to the battery 18, on/off switch 20, speaker 24, shock button 28, microphone 34, and data card 36, the AED base unit 44 includes a receptacle 58 and a connector 60 for respectively receiving the cartridge 46 and the connector 54. The base unit 44 may read the information provided by the groove 57 using conventional techniques or a technique such as that disclosed in U.S. patent application Ser. No. 09/746,123, entitled CARTRIDGE FOR STORING AN ELECTRODE PAD AND METHODS FOR USING AND MAKING THE CARTRIDGE, filed on Dec. 22, 2000, which is heretofore incorporated by reference. The connectors 54 and 60, which electrically interconnect the cartridge assembly 42 and the base unit 44, may be the sole means by which the cartridge assembly and the base unit are attached to one another. Alternatively, means such as Velcro® strips (not shown), mating grooves (not shown) in the side walls of the receptacle 58 and the side walls 50b and 50d of the cartridge 46, or other conventional means may be included to attach the cartridge 46 to the base unit 44. Furthermore, the manufacturer may permanently attach the cartridge 46 to the base unit 44 to prevent one from taking the modular AED system 40 apart. One would, however, be able to replace the pads 16a and 16b without replacing the cartridge 46. Or, the manufacturer may allow one to remove the cartridge 46 from the base unit 44 such that he/she can replace the cartridge assembly 42 with another cartridge assembly or module (not shown in FIG. 2).

Furthermore, the AED base unit 44 may include a compartment 62 for storing defibrillator electrode pads, such as the pads 16a and 16b, when a module other than the cartridge assembly 42 is in the receptacle 58. The connector 60 or another connector (not shown) may connect the pads in the compartment 62 to the base unit 44. In addition, the compartment 62 may include a lid or other cover (not shown).

The operation of the modular AED system 40 is discussed according to an embodiment of the invention. During an emergency where it is determined that a patient (not shown) may need a shock, the operator (hands shown in FIG. 2) retrieves the AED base unit 44 and installs the battery 18 if it is not already installed. Next, the operator inserts the connector 54 into the connector 60, and thus inserts the cartridge 46 into the receptacle 58, if the cartridge 46 is not already installed. Then, the operator opens the lid 52 and removes the electrode pads 16*a* and 16*b* from the cartridge 46. Next, the operator activates the base unit 44 by turning the on/off switch 20 to the "on" position, and in response to written or spoken instructions, places the electrode pads 16*a* and 16*b* on the patient (not shown). The base unit 44 then analyzes the patient's ECG to determine whether the patient is suffering from a shockable heart rhythm. If the base unit 44 determines that the patient is suffering from a shockable heart rhythm, it then instructs the operator to press the shock button 28. Conversely, if the base unit 44 determines that the patient is not suffering from a shockable heart rhythm, it may inform the operator to seek appropriate non-shock treatment for the patient and may disable the shock button 28. After the operator has treated the patient, he/she typically installs new pads 16*a* and 16*b* or an entire new cartridge assembly 42. Thus, with new pads or a new cartridge assembly installed, the modular AED system 40 is ready for its next use. Alternatively, one may wait until the next use of the AED system 40 to install new pads or a new cartridge assembly.

Although the modular AED system 40 is discussed, other modular medical devices or systems are contemplated. Furthermore, although the AED system 40 is discussed having a pair of pads 16*a* and 16*b*, the system may have more or fewer pads. Or, the system 40 may be capable of, and include pads that are suitable for, electrotherapies other than or in addition to defibrillating. Such electrotherapies may include monitoring, cardioverting, or pacing. Moreover, the system 40 may include a manual override that allows the operator (hands shown in FIG. 2) more control over otherwise automated functions. In one embodiment, the modular system 40 is configured with a certain set of one or more modules (such as the cartridge assembly 42) in conjunction with the base unit 44. This configuration is typically determined by the type of AED features the customer/operator desires or the particular model of the AED system 40 that the manufacturer produces. Such a configure-to-order (CTO) scenario allows the customer/operator to choose a modular AED system 40 having the features and functionality he/she needs.

Figure 3:
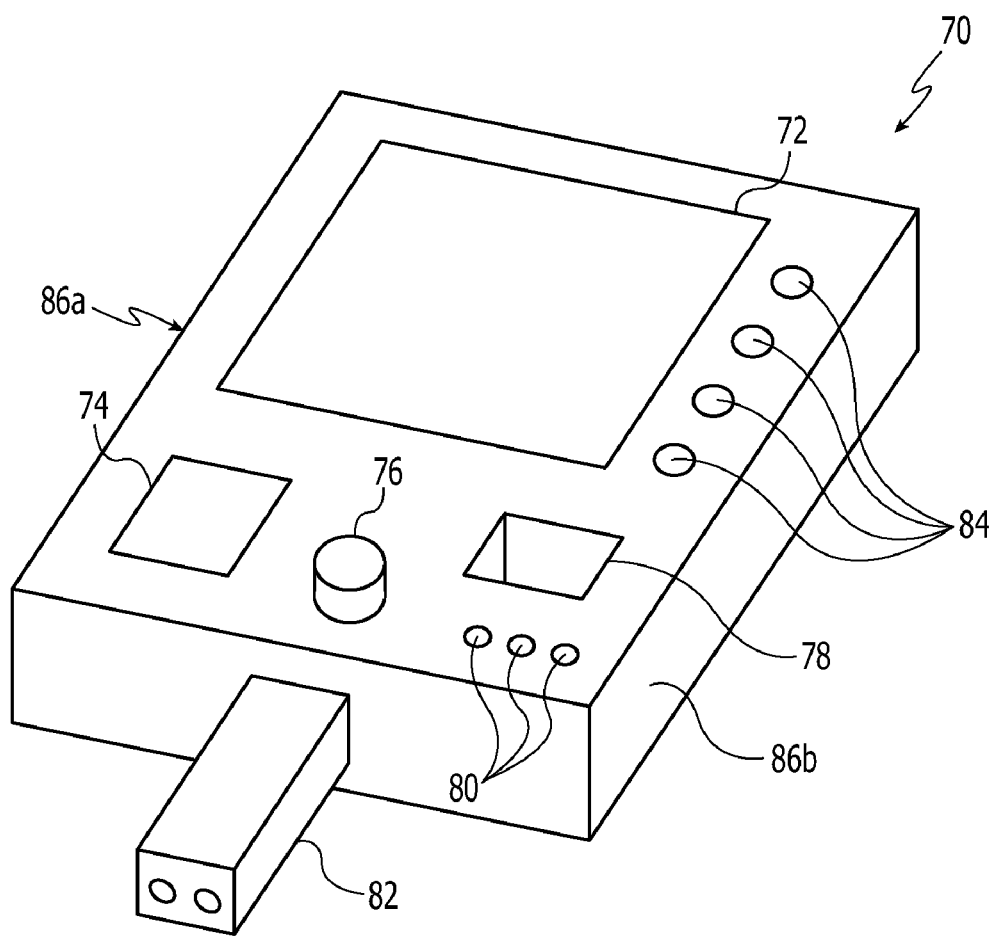
FIG. 3 is a view of a control module that can replace the pad-cartridge module of FIG. 2 according to an embodiment of the invention.

FIG. 3 is a control module 70 that can replace the cartridge assembly 42 of FIG. 2 according to an embodiment of the invention. The manufacturer may give an operator (not shown in FIG. 3) the ability to configure the AED system 40 (FIG. 2) to meet his/her needs. Specifically, the operator can configure the system 40 by inserting the module 70 into the receptacle 58 (FIG. 2) of the AED base unit 44 (FIG. 2) in place of the cartridge assembly 42. The module 70 typically receives power from the base unit 44, and provides additional features to the modular AED system 40 (FIG. 2) as described below.

The control module 70 includes a display 72, status indicator 74, control knob 76, pad connector 78, indicator light-emitting diodes (LEDs) 80, a connector 82, and push buttons 84. The display 72 displays operator information such as patient-treatment instructions or an AED function-select menu. The indicator 74 and LEDs 80 provide the status of the AED 40. For example, the indicator 74, LEDs 80, or both may indicate when the shock circuitry (FIG. 8) is ready to deliver a shock to the patient (not shown). The control knob 76 allows the operator to manipulate the display 72. For example, the operator may control the brightness or contrast of the display 72 by turning the knob 76. The connector 78 allows one to connect a set of pads, such as the pads 16*a* and 16*b* (FIG. 2), to the AED system 40. The connector 82 is similar to the connector 54 (FIG. 2) and mates with the base-unit connector 60 (FIG. 2). Although not shown, the connector 82 may include an information provider such as the groove 57 (FIG. 2). The push buttons 84 allow the operator to select software-menu items from the display 72, or may provide other features. Alternatively, the display 72 may include a touch-sensitive screen so that the manufacturer can omit the buttons 84.

Other embodiments of the control module 70 may have a different layout or different controls, or may provide different features. For example, the positions of the display 72, status indicator 74, selection knob 76, pad connector 78, indicator LEDs 80, connector 82, and push buttons 84 may be rearranged. Furthermore, the knob 76 may control defibrillation functions other than the brightness or contrast of the display 72. For example, the knob 76 may control the level of the shock energy or the volume of the speaker 24 (FIG. 2). Furthermore, these components may be replaced with equivalent components. For example, although the pad and module connectors 78 and 82 are respectively shown as female and male connectors, they may be male and female connectors. Or the knob 76 or buttons 84 may be replaced with other types of control components such as switches. In addition, the display 72 may provide the status of the AED system 40 so that the manufacturer can omit the status indicator 74 or LEDs 80. Moreover, although the connectors 82 and 60 (FIG. 2) may be the sole means by which the module 70 is attached to the base unit 44 (FIG. 2), means such as, screws, fasteners, or Velcro strips (not shown), mating grooves (not shown) in the side walls of the receptacle 58 and the side walls 86*a* and 86*b* of the module 70, or other conventional means may be included to attach the module 70 to the base unit 44. Furthermore, the module 70 may provide power to the base unit 44. In addition, the manufacturer may permanently attach the module 70 to the base unit 44 to prevent one from taking the modular AED system 40 apart. Or, the manufacturer may allow one to remove the module 70 from the base unit 44 such that he/she can replace the module with another module or the cartridge assembly 42 (FIG. 2).

Figure 4:
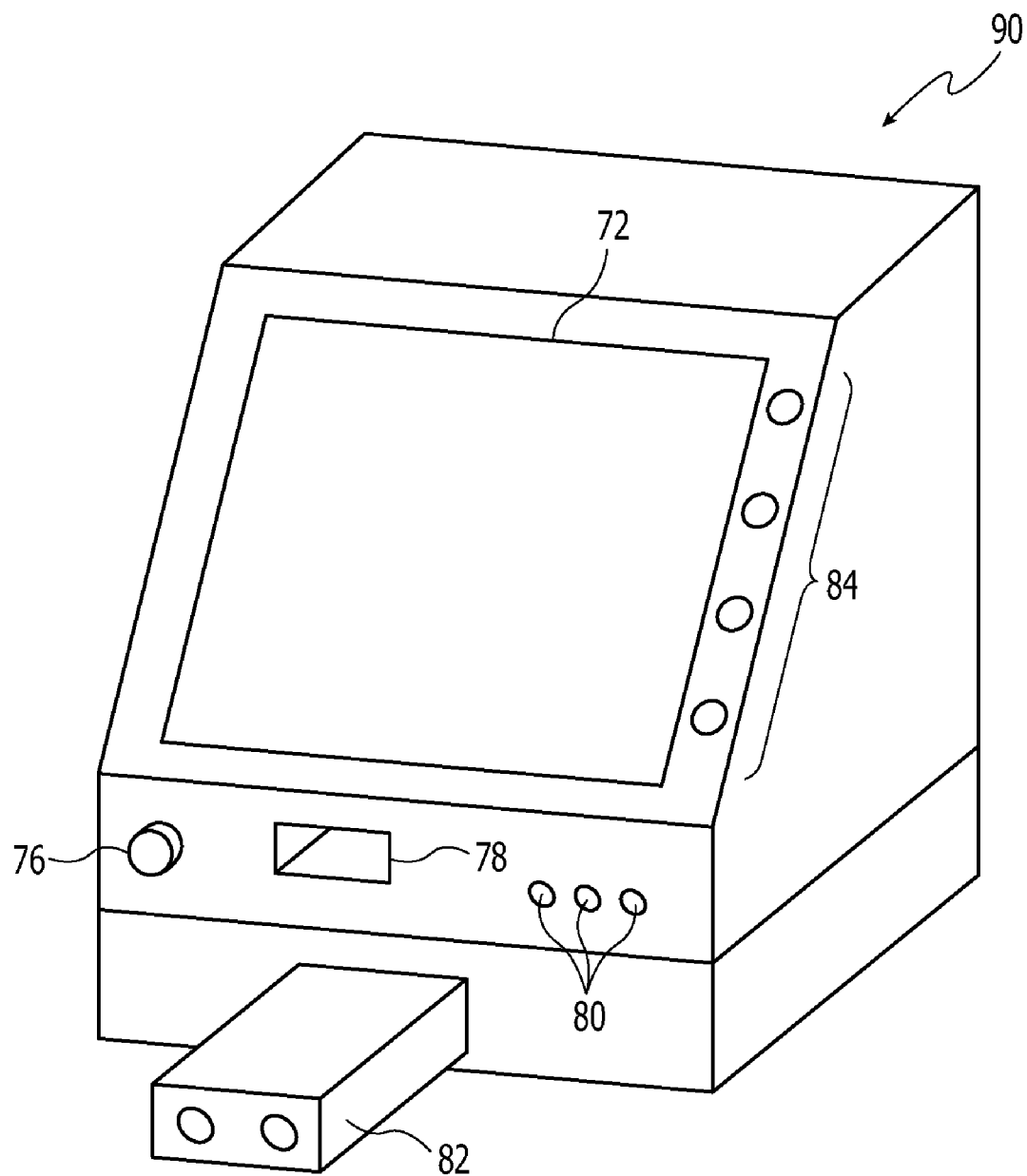
FIG. 4 is a view of a monitor module that can replace the pad-cartridge module of FIG. 2 according to an embodiment of the invention.

FIG. 4 is a monitor module 90 that can replace the cartridge assembly 42 of FIG. 2 according to an embodiment of the invention, where like numbers identify like components with respect to the control module 70 of FIG. 3. Specifically, an operator (not shown in FIG. 4) can insert the module 90 into the receptacle 58 (FIG. 2) of the base unit 44 in place of the cartridge assembly 42. The module 90 typically receives power from the base unit 44, and provides additional features to the modular AED system 40 (FIG. 2) as described below.

Like the control module 70 of FIG. 3, the monitor module 90 includes a display 72, control knob 76, pad connector 78, indicator light-emitting diodes (LEDs) 80, connector 82, and push buttons 84. The display 72 displays information such as patient-treatment instructions, an AED function-select menu, or a patient waveform such as the patient's electrocardiogram (ECG). The display 72 may also display the status of the AED system 40 (FIG. 2).

Other embodiments of the monitor module 90 are contemplated. These embodiments may incorporate modifications similar to those discussed above in conjunction with FIG. 3 for the other embodiments of the control module 70.

Figure 5:
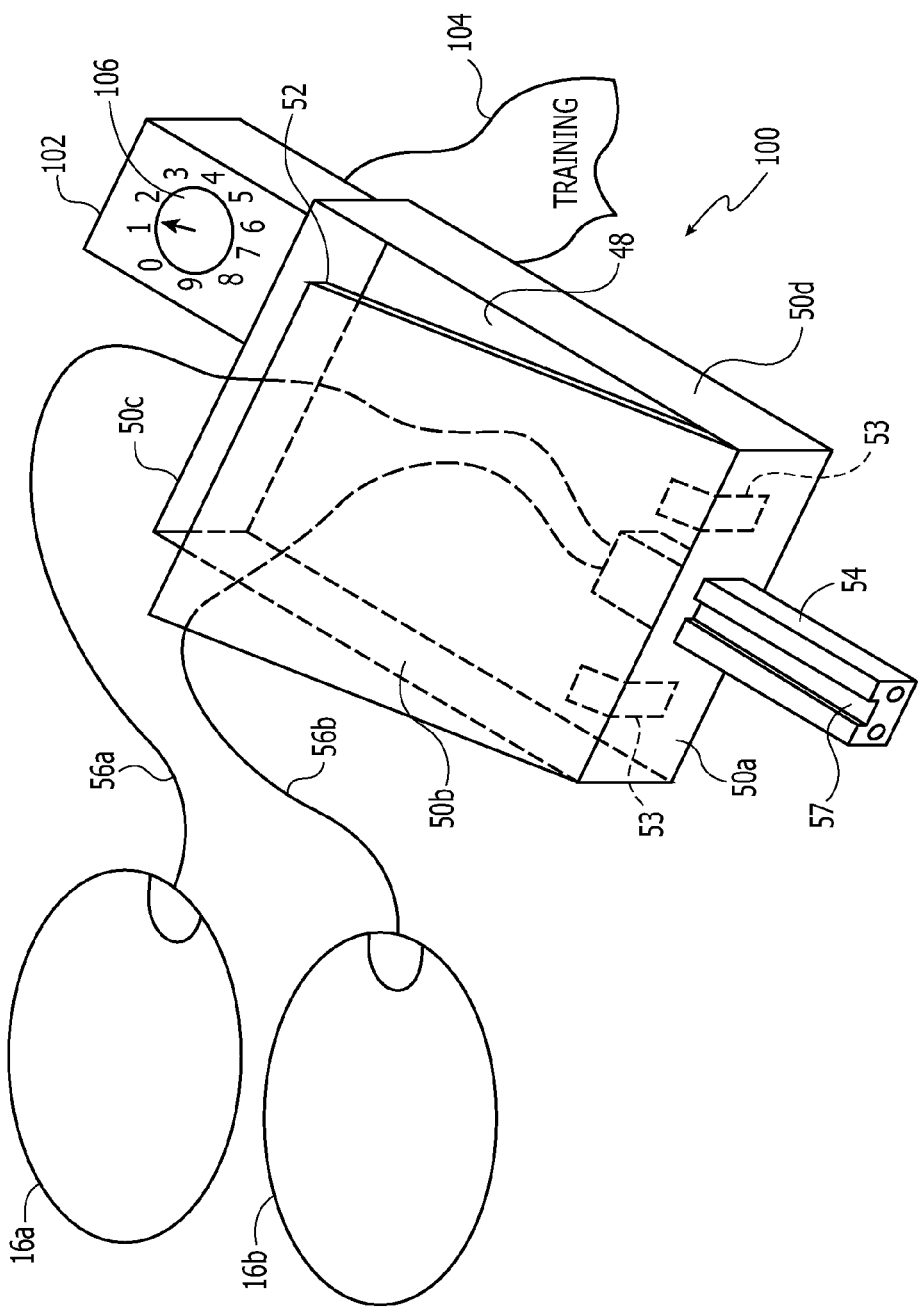
FIG. 5 is a view of a training-pad-cartridge module that can replace the pad-cartridge module of FIG. 2 according to an embodiment of the invention.

FIG. 5 is a training cartridge assembly 100 that can replace the cartridge assembly 42 of FIG. 2 according to an embodiment of the invention, where like numbers identify like components with respect to the cartridge assembly 42. Specifically, an operator (not shown in FIG. 5) can adjust the training-scenario selector 102 to simulate any of a number of different rescue or training scenarios. If power is needed, the selector 102 typically receives it from the base unit 44, and provides training features to the modular AED system 40

(FIG. 2) as described below. Alternatively, the cartridge assembly 100 may have its own power supply (not shown) such as a battery.

The cartridge assembly 100 is similar to the cartridge assembly 42 of FIG. 2 except that it includes the training-scenario selector 102, and, to prevent accidental shock delivery, the connector 54 does not electrically couple the electrode pads 16a and 16b to the base unit 44 (FIG. 2). Furthermore, to prevent inadvertent use of the assembly 100 during an actual rescue, an optional flag 104 indicates that the assembly 100 is a training assembly.

In operation, an operator (not shown in FIG. 5) sets a selector knob 106 of the selector 102 to a desired training scenario that allows him/her to train a student (not shown) in the use of the AED system 40 (FIG. 2). For example, the operator can set the knob 106 so that the selector 102 causes the AED base unit 44 to behave as if it has determined that a patient (not shown) is suffering from a shockable heart condition. Then, while the operator studies and comments on his/her performance, the student tries to revive the patient using the AED system 40. For such training purposes, the patient can be a mannequin. AED training devices and techniques are further discussed in U.S. Pat. Nos. 5,611,815, 5,662,690, and 5,993,219, which are incorporated by reference.

Figure 6:
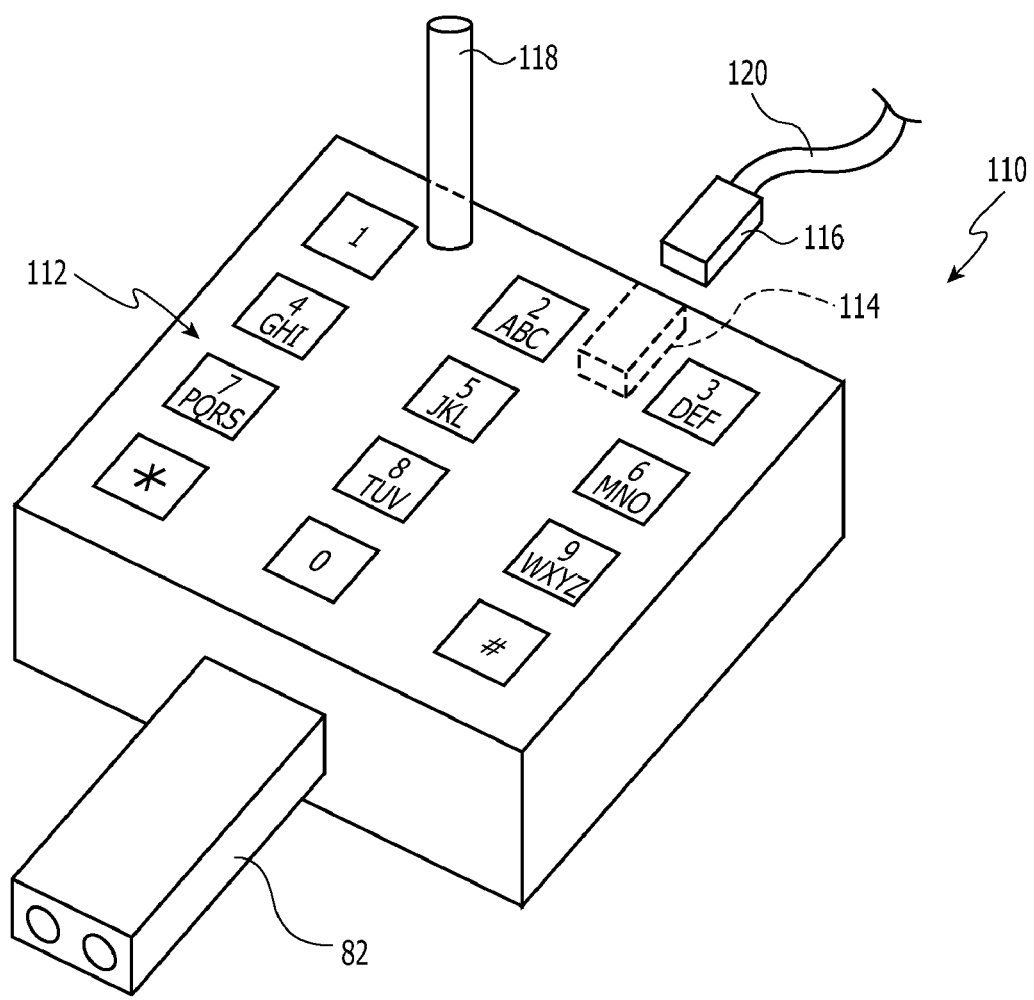
FIG. 6 is a view of a communication module that can replace the pad-cartridge module of FIG. 2 according to an embodiment of the invention.

FIG. 6 is a communication module 110 that can replace the cartridge assembly 42 of FIG. 2 according to an embodiment of the invention, where like numbers identify like components with respect to the monitor module 90 of FIG. 4. Specifically, an operator (not shown in FIG. 6) can insert the module 110 into the receptacle 58 (FIG. 2) of the AED base unit 44 in place of the cartridge assembly 42. The module 110 typically receives power from the base unit 44, and provides additional features to the modular AED system 40 (FIG. 2) as described below.

In addition to a base-unit connector 82, the communication module 110 includes a conventional telephone keypad 112, female telephone connector 114 for receiving a male connector 116, and an optional antenna 118. After completion of the patient-rescue operation, the operator (not shown in FIG. 6) connects the connector 114 to the connector 116 and dials the telephone number of a data-collection center (not shown). Then, the AED base unit 44 (FIG. 2) uses the module 110 as a modem to download rescue data from the card 36 (FIG. 2) or from the base unit in general to the data-collection center via a phone line 120. Alternatively, the base unit 44 uses the module 110 as a wireless modem to download the rescue data via the antenna 118 and a wireless channel. The base unit 44 may also receive data from the data-collection center via the telephone line 120 or the wireless channel. Other functions of the module 110 include downloading new or updated software for the base unit 44, module 110, or both, or downloading rescue instructions for the operator. Other embodiments of the monitor module 110 are contemplated. These embodiments may incorporate modifications similar to those discussed above in conjunction with FIG. 3 for the other embodiments of the control module 70.

Figure 7:
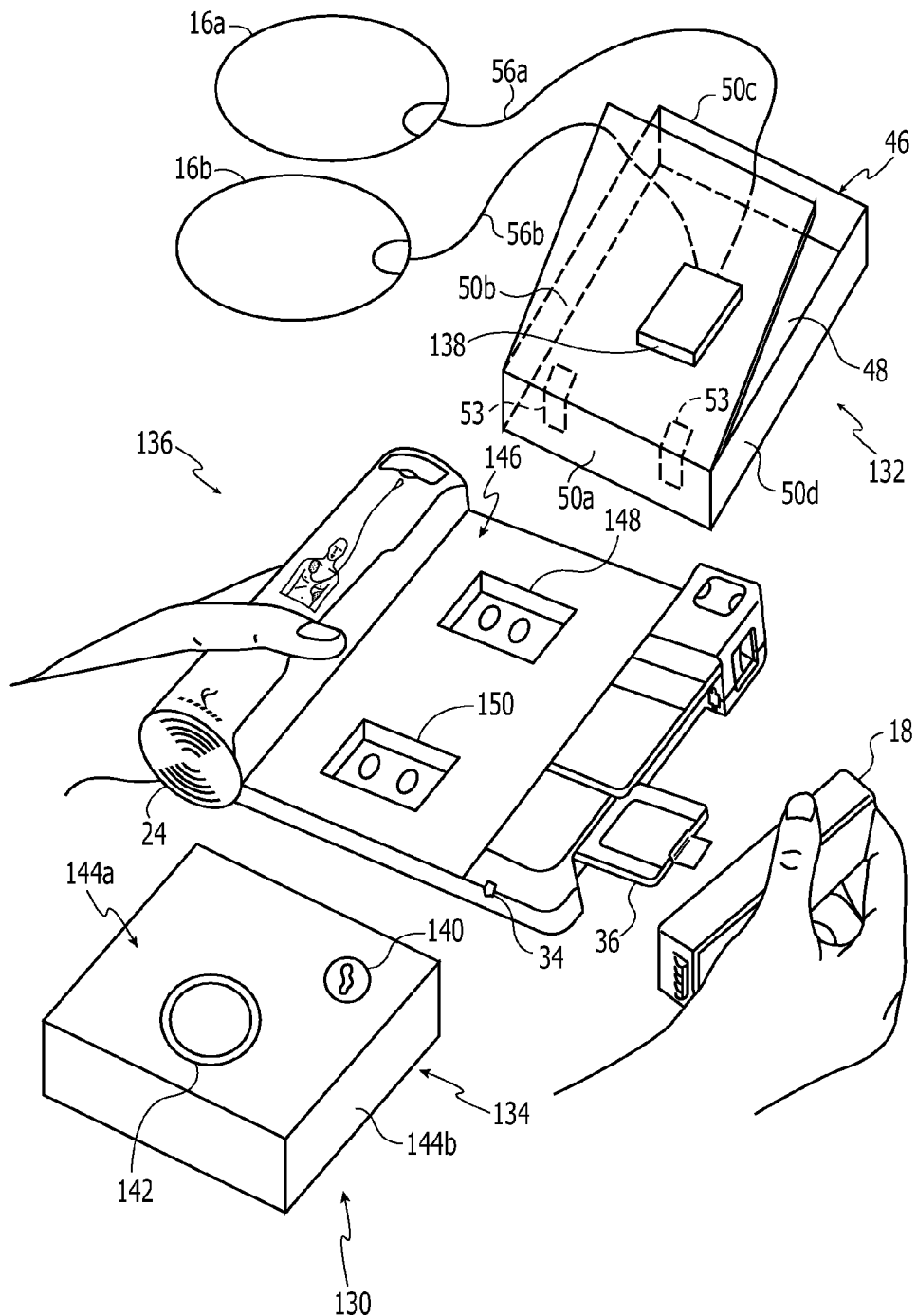
FIG. 7 is an exploded view of another modular AED according to an embodiment of the invention.

FIG. 7 is an exploded view of a modular AED system 130, which includes an electrode-pad module, i.e., cartridge assembly, 132, a control module 134, and an AED base unit 136 according to an embodiment of the invention. For clarity, like numerals refer to elements common to the AED system 40 (FIG. 2). A difference between the AED system 130 and the AED system 40 is that the base unit 136 lacks a shock button and an on/off switch. Therefore, in this embodiment, the AED 130 requires a control module such as the control module 134. In addition, although not shown in FIG. 7, the base unit 136 may include a pad storage compartment such as the storage compartment 62 of the base unit 44 (FIG. 2).

The cartridge assembly 132 includes a connector 138 to which the pads 16a and 16b are connected via the leads 56a and 56b. Unlike the connector 54 (FIG. 2) of the cartridge assembly 42 (FIG. 2), the connector 138 extends through the bottom 48 of the cartridge 46. But like the connector 54, the connector 138 may include an information provider such as the groove 57 (FIG. 2). Otherwise, the cartridge assembly 132 is similar to the cartridge assembly 42.

The control module 134 typically receives power from the AED base unit 136, and includes an on/off switch 140, shock button 142, and side walls 144a and 144b. The switch 140 and button 142 may be similar to the on/off switch 20 and the shock button 28 of FIG. 2, respectively. The module 134 also includes a connector (not shown) that extends from the bottom of the module and that may include an information provider such as the groove 57 (FIG. 2). Other embodiments of the module 134 are contemplated. These embodiments may incorporate modifications similar to those discussed above in conjunction with FIG. 3 for the other embodiments of the control module 70. Furthermore, in addition to the battery 18, speaker 24, microphone 34, and data card 36, the AED base unit 136 includes a receptacle 146 and connectors 148 and 150 for respectively receiving the connector 138 of the cartridge 46 and the connector (not shown) of the control module 134. The base unit 136 may read the information provided by information providers on the connector 138 and the connector of the module 134. The connectors, 138, 148, 150, and the control-module connector, which electrically interconnect the cartridge assembly 132, the control module 134, and the base unit 136, may be the sole means by which the cartridge assembly and the control module are attached to the base unit. Alternatively, other attachment means, such as those described above in conjunction with FIGS. 2 and 3, may be included to attach the cartridge 46 and the module 134 to the base unit 136. Furthermore, the manufacturer may permanently attach the cartridge assembly 132 and the control module 134 to the base unit 136 to prevent an operator (hands shown in FIG. 7) from taking the modular AED system 130 apart. Or, the manufacturer may allow the operator to remove the cartridge assembly 132 or the control module 134 from the base unit 136 such that he/she can replace the cartridge assembly or control module with another cartridge assembly or module (not shown in FIG. 7). Where the cartridge assembly 132 is permanently attached to the base unit 136, the operator can replace the pads 16a and 16b without replacing the cartridge 46.

Still referring to FIG. 7, the operation of the modular AED system 130 is discussed according to an embodiment of the invention. During an emergency where it is determined that a patient (not shown) may need a shock, the operator (hands shown in FIG. 7) retrieves the AED base unit 130 and installs the battery 18 if it is not already installed. Next, the operator inserts the connector 138 into the connector 148, and thus inserts the cartridge 46 into one end of the receptacle 146, if the cartridge 46 is not already installed. Similarly, the operator inserts the control-module connector (not shown) into the connector 150, and thus inserts the control module 134 into the other end of the receptacle 146, if the control module is not already installed. Then, the operator opens the lid 52 and removes the electrode pads 16a and 16b from the cartridge 46. Next, the operator activates the control module 134 and the base unit 136 by turning the on/off switch 140 to the "on" position, and in response to written or spoken (via the speaker 24) instructions, places the electrode pads 16a and 16b on the patient (not shown). The base unit 136 then analyzes the patient's ECG to determine whether the patient is suffering from a shockable heart rhythm. If the base unit 136 determines that the patient is suffering from a shockable heart rhythm, then it instructs the operator to depress the shock button 142. Conversely, if the base unit 136 determines that the patient is not suffering from a shockable heart rhythm, it may inform the operator (e.g., via the speaker 24) to seek appropriate non-shock treatment for the patient and may disable the shock button 142. After the operator has treated the patient, he/she installs new pads 16*a* and 16*b*, or an entire new cartridge assembly 132. Thus, with new pads or a new cartridge assembly installed, the AED system 130 is ready for its next use. Alternatively, the operator may wait until the next use of the system 130 to install a new cartridge assembly or pads. Typically, the operator does not detach the control module 134 from the base unit 136 once the control module is installed.

Figure 8:
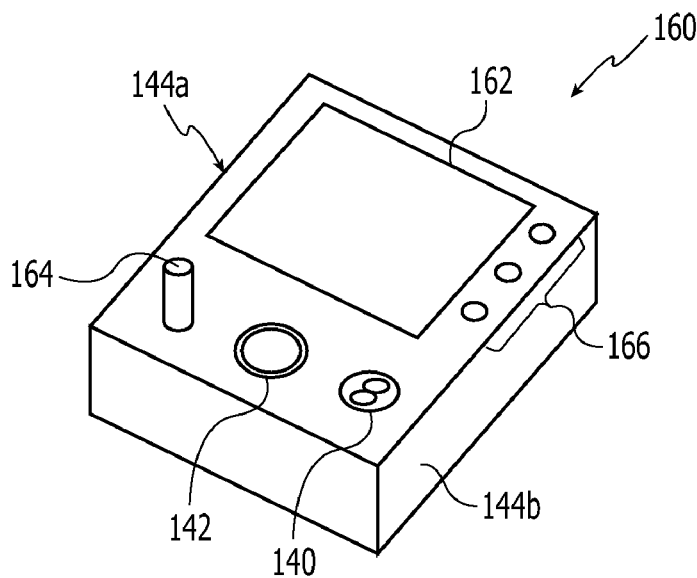
FIG. 8 is a view of an enhanced control module that can replace the control module or the pad-cartridge module of FIG. 7 according to an embodiment of the invention.

FIG. 8 is an enhanced control module 160 that can replace the cartridge assembly 132 or the control module 134 of FIG. 7 according to an embodiment of the invention, where like numbers reference like components with respect to the control module 134. Typically, an operator (not shown in FIG. 8) inserts the module 160 into the base-unit receptacle 146 (FIG. 7) in place of the control module 134. The control module 160 has more features than the control module 134 as described below.

The control module 160 typically receives power from the AED base unit 136 (FIG. 7), and, in addition to the on/off switch 140 and shock button 142, includes a display 162, control knob 164, and push buttons 166, which are respectively similar to the display 72, control knob 76, and push buttons 84 of FIG. 3. The module 160 also includes a connector (not shown) that extends from its bottom and that mates with the connector 150 (FIG. 7) of the base unit 136. This connector may include an information provider such as the groove 57 (FIG. 2).

Other embodiments of the control module 160 are contemplated. These embodiments may incorporate modifications similar to those discussed above in conjunction with FIG. 3 for the other embodiments of the control module 70.

Figure 9:
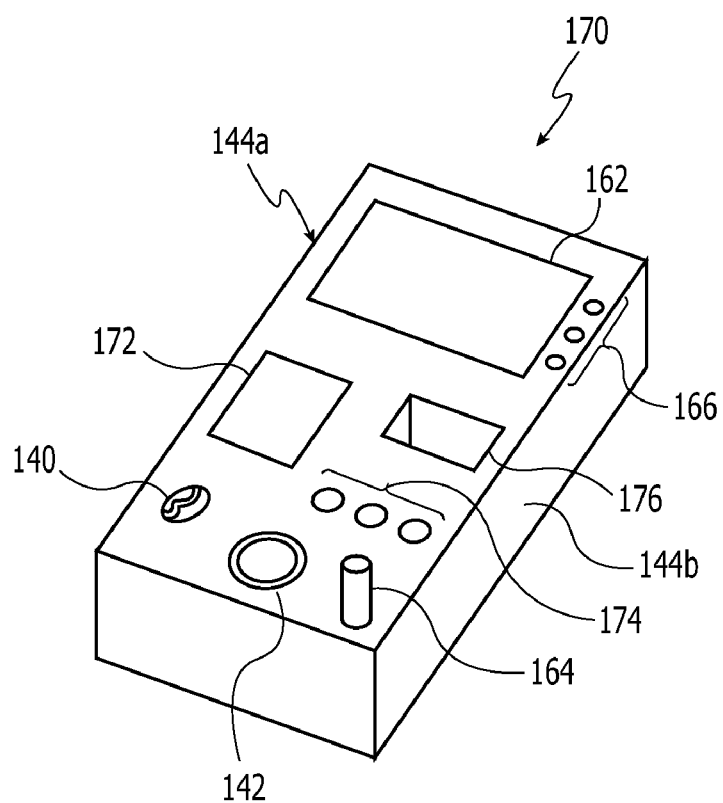
FIG. 9 is a view of a full-featured control module that can replace one or both of the control module and pad-cartridge module of FIG. 7 according to an embodiment of the invention.

FIG. 9 is a full-featured control module 170 that can replace one or both of the cartridge assembly 132 and the control module 134 of FIG. 7 according to an embodiment of the invention, where like numbers reference like components with respect to the control module 160 (FIG. 8). Typically, the module 170 is sized to occupy the entire base-unit receptacle 146 (FIG. 7). Therefore, the operator (not shown in FIG. 9) inserts the module 170 into the base-unit receptacle 146 in place of the cartridge assembly 132 and the control module 134. The control module 170 has more features than the enhanced control module 160 as described below.

The control module 170 typically receives power from the AED base unit 136 (FIG. 7), and, in addition to the on/off switch 140, shock button 142, display 162, control knob 164, and push buttons 166, includes a status indicator 172, indicator LEDs 174, and a pad connector 176, which are respectively similar to the status indicator 74, LEDs 80, and pad connector 78 of FIG. 3. The module 170 also includes a pair of connectors (not shown) that extend from its bottom and that respectively mate with the connectors 148 and 150 of the base unit 136. One or both of these connectors may include an information provider such as the groove 57 (FIG. 2). Alternatively, the module 170 may include a single connector (not shown) that extends from the its bottom and that mates with one of the connectors 148 and 150 of the base unit 136.

Other embodiments of the control module 170 are contemplated. These embodiments may incorporate modifications similar to those discussed above in conjunction with FIG. 3 for the other embodiments of the control module 70. Furthermore, the module 170 may be sized to occupy only a portion of the base-unit receptacle 146 (FIG. 7) such that the cartridge assembly 132 or another module (not shown) can simultaneously occupy the receptacle 146 with the module 170.

Figure 10:
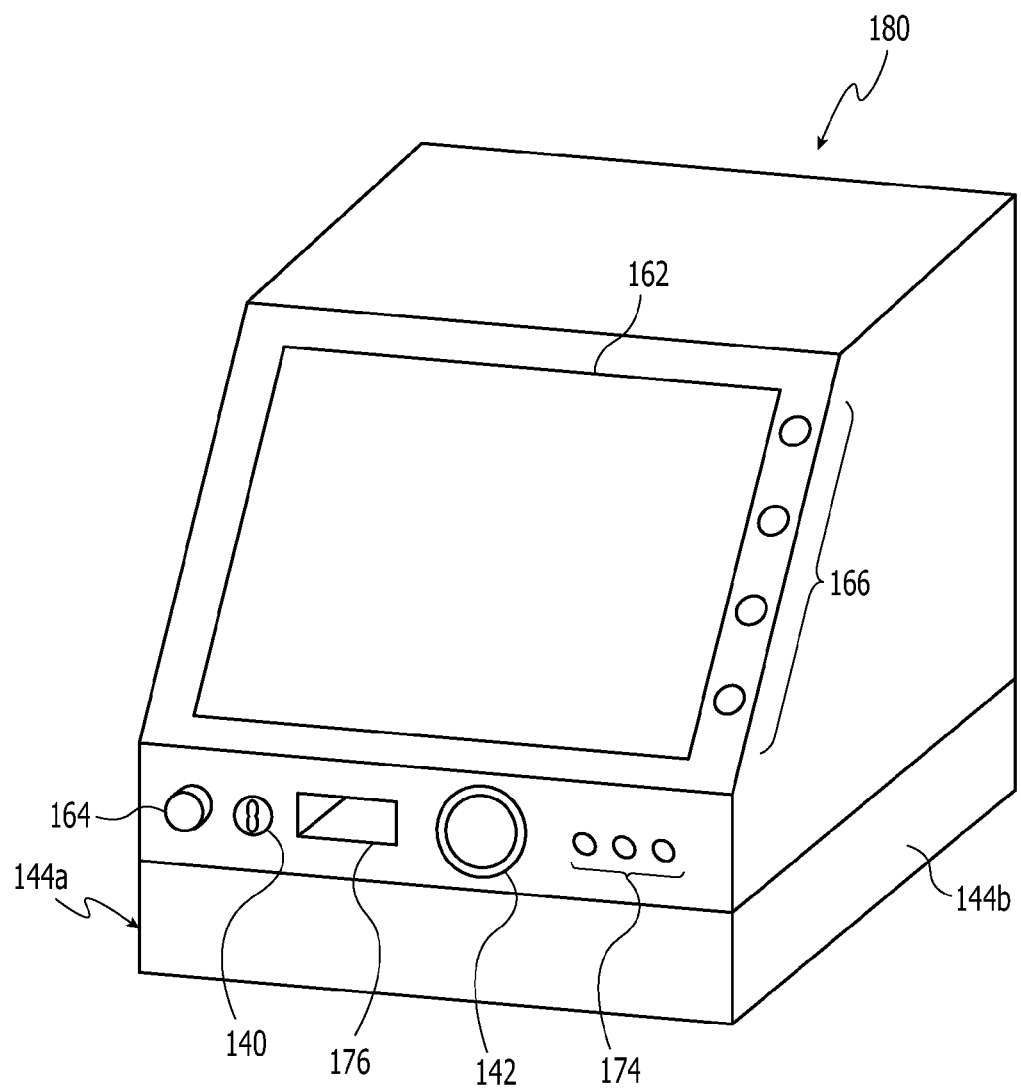
FIG. 10 is a view of a monitor module that can replace one or both of the control module and pad-cartridge module of FIG. 7 according to an embodiment of the invention.

FIG. 10 is a monitor module 180 that can replace one or both of the cartridge assembly 132 and the control module 134 of FIG. 7 according to an embodiment of the invention, where like numbers identify like components with respect to the control module 170 (FIG. 9). Typically, the module 180 is sized to occupy the entire base-unit receptacle 146 (FIG. 7). Therefore, the operator (not shown in FIG. 10) inserts the module 180 into the receptacle 146 of the base unit 136 in place of the cartridge assembly 132 and the control module 134. The module 180 typically provides additional features to the modular AED system 130 (FIG. 7) as described below.

The monitor module 180 typically receives power from the AED base unit 136 (FIG. 7), and includes on/off switch 140, shock button 142, display 162, control knob 164, push buttons 166, indicator light-emitting diodes (LEDs) 174, and pad connector 176. The display 162 displays information such as patient-treatment instructions, an AED function-select menu, or a patient waveform such as the patient's electrocardiogram (ECG). The display 162 may also display the status of the AED 130. Furthermore, the module 180 may include a single connector (not shown) that extends from the bottom of the module and that mates with one of the base-unit connectors 148 or 150 (FIG. 7). Alternatively, the module 180 may include two such connectors that each mate with a respective one of the base-unit connectors 148 and 150. One or both of these connectors may include an information provider such as the groove 57 (FIG. 2).

Other embodiments of the monitor module 180 are contemplated. These embodiments may incorporate modifications similar to those discussed above in conjunction with FIG. 3 for the other embodiments of the control module 70. Furthermore, the module 180 may be sized to occupy only a portion of the base-unit receptacle 146 (FIG. 7) such that the cartridge assembly 132 or another module (not shown) can simultaneously occupy the receptacle 146 with the module 180.

Figure 11:
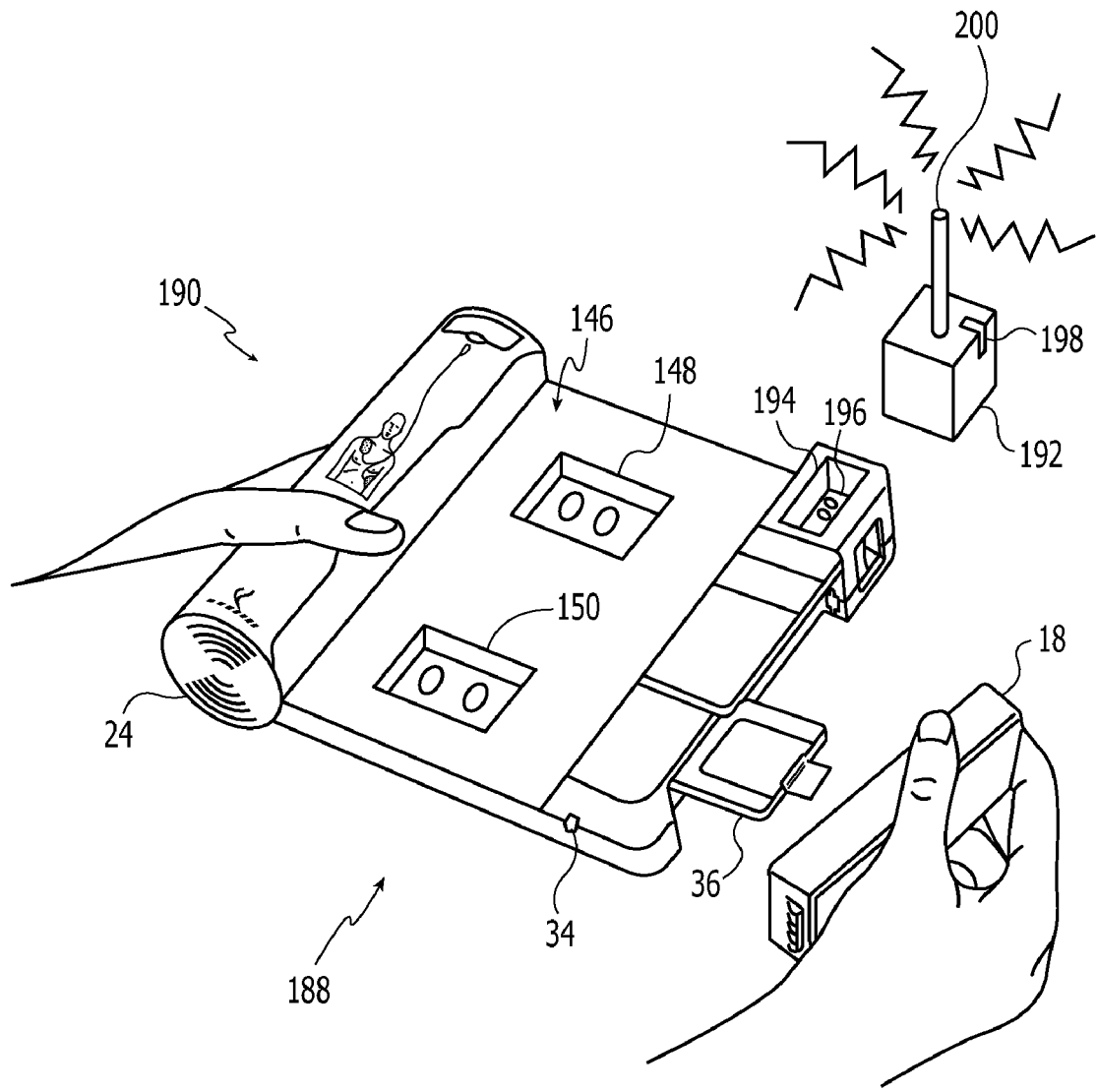
FIG. 11 is an exploded view of yet another modular AED according to an embodiment of the invention.

FIG. 11 is a modular AED system 188, which includes an AED base unit 190 and communication module 192 according to an embodiment of the invention, where like numbers identify like components with respect to the AED system 130 (FIG. 7).

The base unit 190 is similar to the base unit 136 except that it includes a receptacle 194 for receiving the communication module 192. The receptacle 194 includes a connector 196 for mating with a corresponding connector (not shown) on the bottom of the module 192.

The communication module 192 allows an operator (hands shown in FIG. 11) to communicate with someone, such as a doctor (not shown), at a remote location, such as a hospital (not shown), before, during, or after a rescue operation. The module 192 includes a microphone 198 for picking up the operator's voice, an antenna 200, which allows wireless communication between the operator and the remote location, and an optional speaker 201. The speaker 24, the speaker 201, or both the speakers 24 and 201 may allow the operator to hear the voice of a person at the remote location. The module 192 may receive power from the base unit 190, or may include a power supply such as a battery (not shown). Furthermore, where the wireless communication is over a wireless telephone network, the base unit 190 or module 192 includes circuitry (not shown) for dialing a predetermined telephone number. The base unit 190 or module 192 may cause the this circuitry to dial the telephone number automatically when the operator powers on the base unit, or may wait for a specific instruction from the operator.

Alternate embodiments of the base unit 190 and module 192 are contemplated. For example, the module 192 may include a telephone keypad and telephone line connector like the module 112 (FIG. 6). In such an embodiment, the module 192 can be used for voice communications and for downloading rescue data as discussed above in conjunction with FIG. 6. Furthermore, the module 192 may include a speaker separate from the speaker 24 to allow the operator to hear the voice of a person at the remote location. In addition, the module 192 may lack the microphone 198, and the microphone 34 may pick up the operator's voice for transmission to the remote location. Moreover, the microphone 198, the antenna 200, the communication circuitry (not shown) within the module 192, and other components (not shown) of the module 192 may be integral with the base unit 190. Furthermore, the AED base unit 44 of FIG. 2 can be modified to receive the module 192. In addition, other embodiments may incorporate modifications similar to those discussed above in conjunction with FIG. 3 for the other embodiments of the control module 70.

Figure 12:
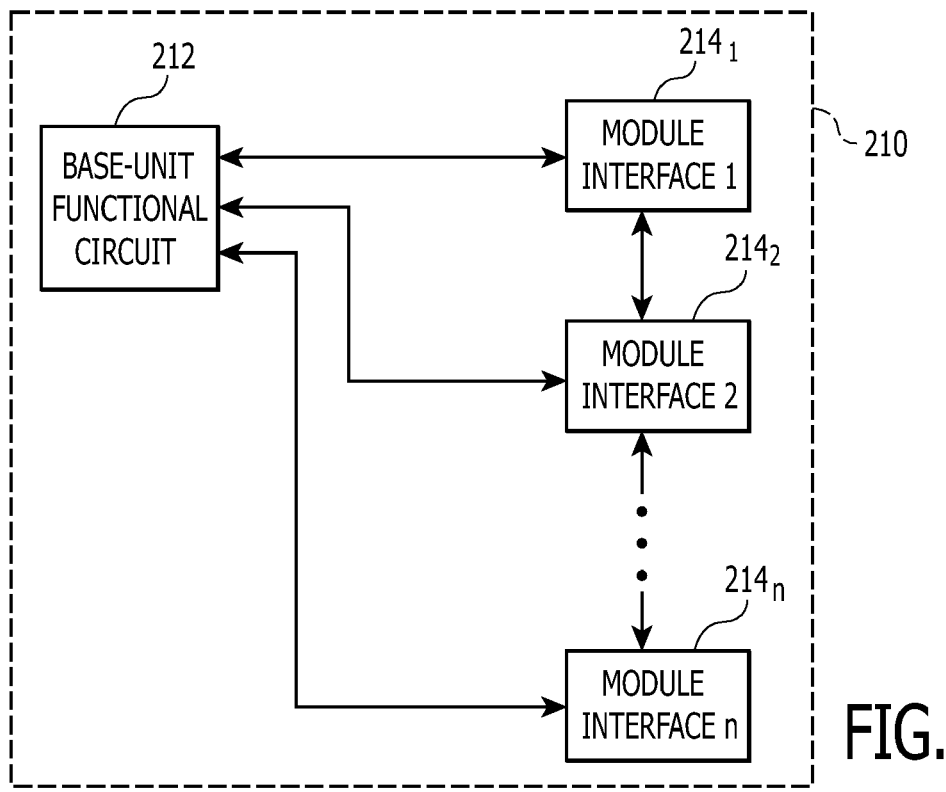
FIG. 12 is a circuit-block diagram of the AED base units of FIGS. 2, 7, and 11 according to an embodiment of the invention.

FIG. 12 is a schematic block diagram of a base-unit circuit 210, which the base units 44 (FIG. 2), 136 (FIG. 7), and 190 (FIG. 11) may incorporate according to an embodiment of the invention. The circuit 210 includes a functional circuit 212 and one or more—here n—module interfaces 214. The functional circuit 212 may include and execute software, and performs functions such as turning on and off the modular AEDs 40, 130, and 188, analyzing a patient's heart rhythm and determining whether it is a shockable rhythm, generating a defibrillation shock if the rhythm is shockable, and sending rescue data to a remote location directly or via a module such as the control module 110 (FIG. 6). The circuit 212 may also control the speaker 24 and the microphone 34, interface with the data card 36, and manage the power supply for the base unit and any connected control modules. Each module interface 214 interfaces the functional circuit 212 to a respective module such as the control module 134 (FIG. 7). Each interface 214 typically includes at least one connector such as the connector 150 (FIG. 7), and may include an interface circuit (not shown). For example, the base unit 136 (FIG. 7) may include a single module interface 214 having the two connectors 148 and 150, or may include two interfaces 214 each having a respective one of the connectors 148 and 150.

Figure 13:
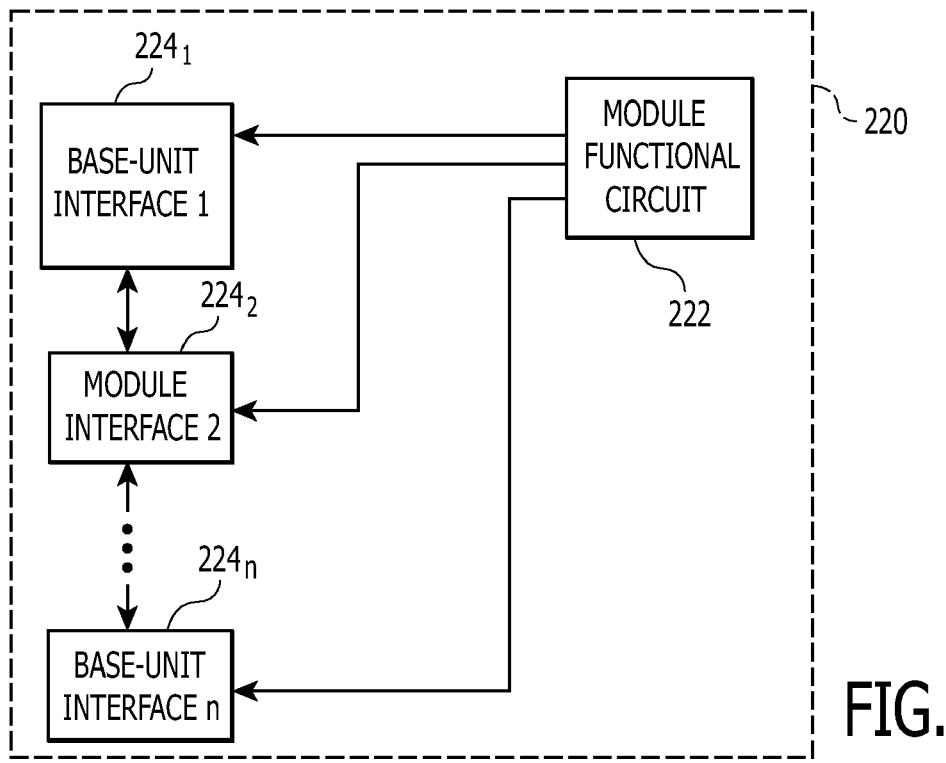
FIG. 13 is a circuit-block diagram of the AED modules of FIGS. 2-6. and 8-11 according to an embodiment of the invention.

FIG. 13 is a schematic block diagram of a module circuit 220, which the modules 42 (cartridge assembly of FIG. 2), 70 (FIG. 3), 90 (FIG. 4), 100 (training cartridge assembly of FIG. 5), 110 (FIG. 6), 132 (cartridge assembly) and 134 (FIG. 7), 160 (FIG. 8), 170 (FIG. 9), 180 (FIG. 10), and 192 (FIG. 11) may incorporate according to an embodiment of the invention. The circuit 220 includes a functional circuit 222 and one or more—here n—base-unit interfaces 224. The functional circuit 222 may include and execute software, and performs functions such as turning on and off the modular AED systems 130 and 188 (FIGS. 7 and 11), controlling the display of information from the base unit (e.g., base unit 136 of FIG. 7) on a display screen (e.g., display screen 72 of FIG. 3), allowing an operator to select menu items or AED functions from the display screen (e.g. via buttons 84 of FIG. 3), providing a status of the AED (e.g., via indicator 74 or LEDs 80 of FIG. 3), instructing the base unit to deliver a shock in response to an operator (not shown in FIG. 13) pushing the shock button 142 (FIGS. 7-10), and dialing a telephone number (e.g., via the key pad 112 of FIG. 6). Each base-unit interface 224 interfaces the module functional circuit 222 to the base-unit functional circuit 212 (FIG. 12) of a base unit, such as the base unit 136 (FIG. 7), via one or more respective module interfaces 214 (FIG. 12). Each base-unit interface 224 typically includes at least one connector such as the connector 82 (FIG. 3), and may include an interface circuit (not shown). For example, the full-featured control module 170 (FIG. 9) may include a single base-unit interface 224 having two connectors (not shown) that respectively mate with the base-unit connectors 148 and 150 (FIG. 7), or may include two interfaces 224 each having a connector that mates with a respective one of the connectors 148 and 150.

Alternatively, for modules such as the cartridge assemblies 42, 100, and 132, of FIGS. 2, 5, and 7 respectively, the functional circuit 212 may be an energy-attenuation circuit, power circuit, or other type of circuit. Or, these modules may altogether omit the functional circuit 212.

Figure 14:
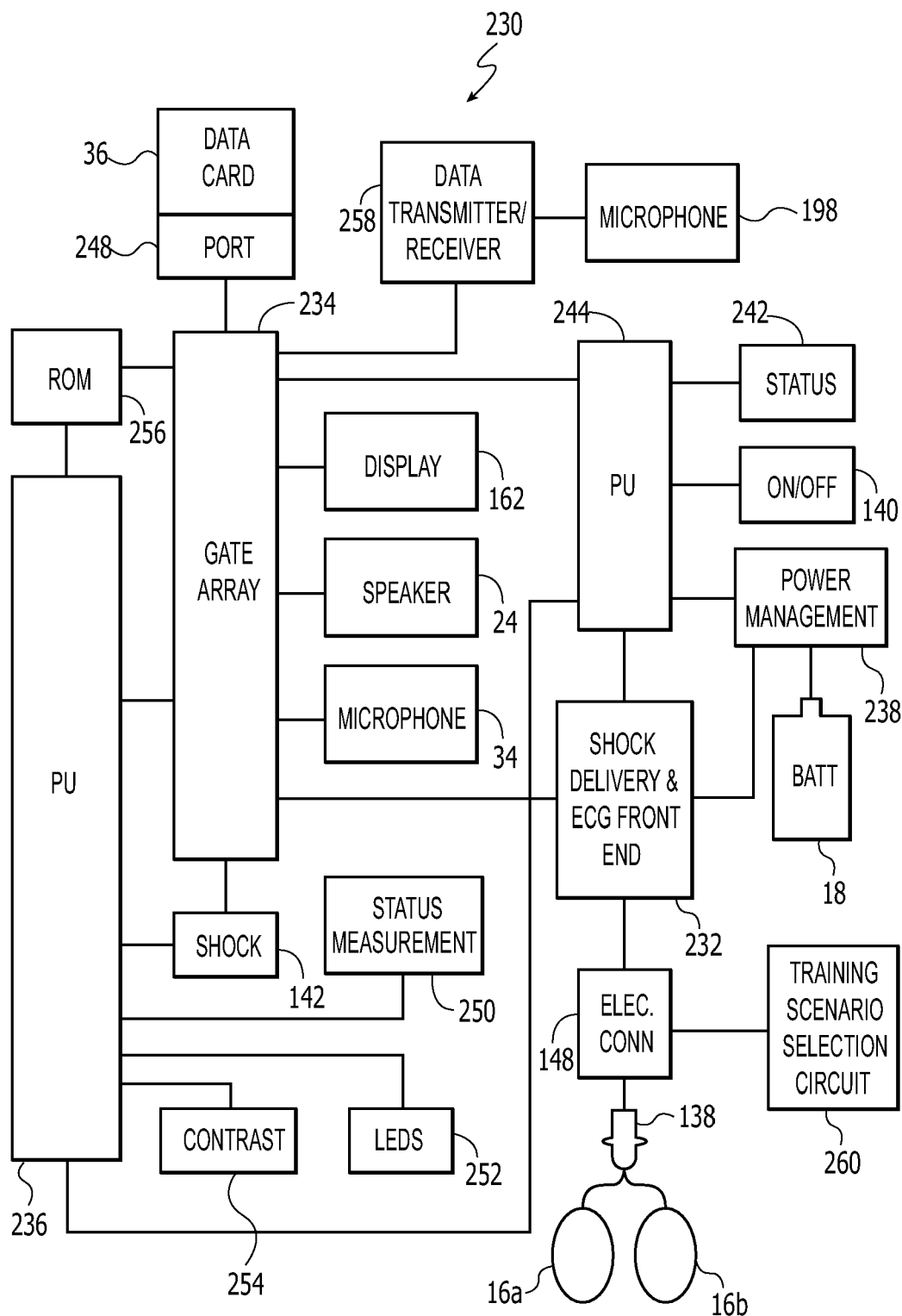
FIG. 14 is a circuit-block diagram of the modular AEDs of FIGS. 2, 7, and 11 according to an embodiment of the invention.

FIG. 14 is a schematic block diagram of an AED circuit 230, which the modular AED systems 40 (FIG. 2), 130 (FIG. 7), and 188 (FIG. 11) can incorporate according to an embodiment of the invention. Table I below gives examples of which of the circuit blocks are disposed in the base unit 44, 136, or 190 and which of the circuit blocks are disposed in the module or modules connected to the base unit. Furthermore, the defibrillator electrode pads 16a and 16b are typically coupled to the base unit via a module. But there is no requirement that a particular circuit block be disposed in the base unit or in a module, or that the pads be connected to or be part of a module. Therefore, circuit blocks disposed in the base unit may be disposed in the module or modules, and vice versa, and the pads may be connected directly to the base unit. For clarity, unless otherwise noted, the AED circuit 230 is described as being part of the modular AED system 130 with the cartridge assembly 132 and the enhanced control module 160 (FIG. 8) attached, it being understood that the circuit 230 is similar when part of the modular AED systems 40 and 188.

Referring to FIG. 14, the defibrillator electrode pads 16a and 16b are coupled to the circuit 230 via the connectors 138 and 148 and are operable to sense a patient's ECG (not shown) and to apply an electrical shock to the patient (not shown). A shock-delivery-and-ECG front-end circuit 232 samples the patient's ECG during an analysis mode of operation, and provides a shock to the patient via the connectors 138 and 148 and the electrode pads 16a and 16b during a shock-delivery mode of operation. A gate array 234 receives the ECG samples from the circuit 232 and provides them to a first processor unit (PU) 236, which stores and analyzes the samples. If analysis of the patient's ECG indicates that the patient is suffering from a shockable heart rhythm, then the processor unit 236 instructs the circuit 232, via the gate array 234, to enable delivery of a shock when an operator (not shown in FIG. 14) presses the shock button 142 (which is coupled to the processor unit 236 via the connector 150 of FIG. 7). Conversely, if analysis of the patient's ECG indicates that the patient is not suffering from a shockable heart rhythm, then the processor unit 236 may disable the circuit 232 from delivering a shock to the patient, and may instruct the operator via the speaker 24 or display 162 to seek non-shock treatment for the patient. Furthermore, the processor unit 236 can detect and signal the operator (e.g., via the speaker 24, the LEDs 252, or status circuit 242) when a module is not coupled to the module connector 148 or 150 (FIG. 7).

The circuit 230 also includes a power-management circuit 238 for distributing power from the battery 18 to the subcircuits of the circuit 230. The on/off switch 140 turns the circuit 230 "on" and "off", a status circuit 242 indicates the status of the circuit 230, and a second processor unit 244 interfaces the power-management circuit 238, the on/off circuit 140 (via the connector 150 of FIG. 7), and the status circuit 242 to the circuit 232, the first processor unit 236, and the gate array 234. As discussed above in conjunction with FIGS. 2-3, the display 162 (comparable to the display 72 of FIG. 3 in one embodiment) displays information to the operator, the speaker 24 provides audio instructions to the operator, and the microphone 34 records the operator's voice and other audible sounds. The data card 36 is connected to the gate array 234 via a port 248. The card 36 stores the operator's voice and other sounds along with the patient's ECG and a record of AED events for later study. Alternatively, another storage device such as magnetic tape (not shown) may store this data. A status-measurement circuit 250 provides the status of the circuit 230 subcircuits to the processor unit 236, and LEDs 252 provide information to the operator such as whether the processor unit 236 has enabled the circuit 232 to deliver a shock to the patient. A contrast control 254, which the operator may manipulate via the control knob 164 (FIG. 8), allows the operator to control the contrast of the display screen 162, and a memory such as a read only memory (ROM) 256 stores programming information for the processor units 236 and 244 and the gate array 234.

Still referring to FIG. 14, the circuit 230 also includes the optional microphone 198, a data transmitter/receiver 258, and a training-scenario selector circuit 260.

As discussed above in conjunction with FIGS. 6 and 11, the transmitter/receiver 258 allows communication of data between the AED circuit 230 and a remote location (not shown) such as a hospital via a landline (FIG. 6) or wireless telephone channel. For example, the transmitter/receiver 258 may receive data from the data card 36 via the gate array 234 and transmit the data to the remote location. Or, the transmitter/receiver 258 may receive voice data from the microphone 34 or 198 and transmit this data to the remote location. Alternatively, the transmitter/receiver 258 may provide data received from the remote location to the processor 236 via the gate array 234. The processor unit 236 may convert the received data into a voice using the speaker 24.

The training-scenario selection circuit 260 allows training of a student in the operation of the AED system 130 (FIG. 7), when the training cartridge assembly 100 is attached to the base unit 136 (FIG. 7) in a manner similar to that discussed above in conjunction with FIG. 5. When the circuit 260 is coupled to the connector 148, the pads 16a and 16b typically are not electrically coupled to the connector 148 to prevent inadvertent delivery of a shock during the training exercise. But the circuit 260 "fools" the processor unit 236 into determining that a selected scenario exists such that the processor unit causes the circuit 230 to operate according to this scenario. For example, the circuit 230 may cause the processor unit 236 to determine that a "patient" is experiencing a shockable heart rhythm, and thus to cause the circuit 230 to operate accordingly. This allows the student to learn the operation of the AED without putting a test patient at risk.

Once can modify the circuit 230 according to known principles such that the AED system 130 can provide electrotherapies other than defibrillation, such as pacing and cardioversion, or includes a manual override that allows an operator (not shown in FIG. 14) more control over otherwise automated functions.

An AED circuit similar to the AED circuit 230 and other AED circuits are further discussed in the following references, which are incorporated by reference: U.S. Pat. Nos. 5,836,993, 5,735,879 entitled ELECTROTHERAPY METHOD AND APPARATUS, U.S. Pat. No. 5,607,454 entitled ELECTROTHERAPY METHOD AND APPARATUS, and U.S. Pat. No. 5,879,374 entitled DEFIBRILLATOR WITH SELF-TEST FEATURES.

Table I describes the locations of the circuit blocks of the AED circuit 230 (FIG. 14) and other circuits and components of the base unit and module(s) according to respective embodiments of the invention. Unless otherwise stated, reference numerals in Table I refer to circuit blocks or components in FIG. 14.

TABLE I (One of Modules 1, 2, and 3 Connected to the Base Unit at a Time)

| Base Unit | Module 1 | Module 2 | Module 3 |
|---|---|---|---|
| Battery 18 | Adult Electrode Pediatric Training Pads 16a and 16b | Pediatric Electrode Pads 16a and 16b | Training Electrode Pads 16a and 16b |
| Speaker 24 | Pad Storage Compartment (not shown, but similar to the compartment 62 of (FIG. 2) | Pad Storage Compartment (not shown, but similar to the compartment 62 of (FIG. 2) | Pad Storage Compartment (not shown, but similar to the compartment 62 of (FIG. 2) |
| On/Off Button 140 | Electrode Pad Connector (e.g., 176 of FIG. 9) | Electrode Pad Connector (e.g., 176 of FIG. 9) | Electrode Pad Connector (e.g., 176 of FIG. 9) |
| Shock Delivery and ECG 232 | Module Identifier Circuit (not shown, identifies type of module to base unit) | Module Identifier Circuit (not shown, identifies type of module to base unit) | Module Identifier Circuit (not shown, identifies type of module to base unit) |
| Gate Array 234 | Module Unconnected (to base unit) Circuit (not shown) | Module Unconnected (to base unit) Circuit (not shown) | Module Unconnected (to base unit) Circuit (not shown) |
| Pus 236 | Module Connector (e.g., connector 82 of FIG. 4) and Base-Unit Interface | Module Connector (e.g., connector 82 of FIG. 4) and Base-Unit Interface | Module Connector (e.g., connector 82 of FIG. 4) and Base-Unit Interface |

TABLE I-continued (One of Modules 1, 2, and 3 Connected to the Base Unit at a Time)

| Base Unit | Module 1 | Module 2 | Module 3 |
|---|---|---|---|
| | Circuitry (e.g., base-unit interface 224 of FIG. 13) | Circuitry (e.g., base-unit interface 224 of FIG. 13) | Circuitry (e.g., base-unit interface 224 of FIG. 13) |
| Power Management 238 | | Energy Attenuation Circuit (not shown) | Module Battery (not shown) |
| Status Measurement 250 LEDs 252 ROM 256 Data Transmitter-Receiver 258 Module Connectors 148 and 150 (and module interface circuitry such as module interface 214 of FIG. 12) | | | Training Scenario Selector 102 (FIG. 5) Including Training-Scenario Selectro Circuit 260 (FIG. 14) |

Figures 15, 16:
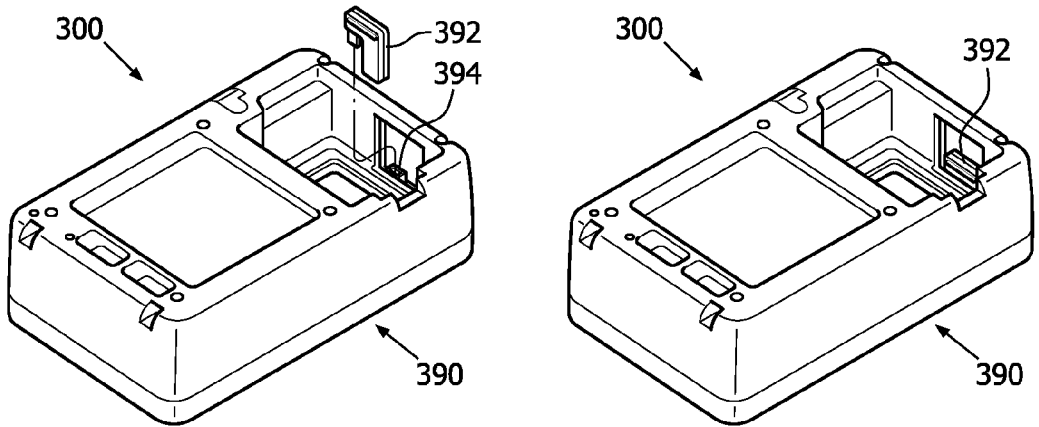
FIG. 15 is a view of yet another modular AED having an communications module installed in the base unit, according to an embodiment of the invention.
FIG. 16 is an exploded view of yet another modular AED and a communications module for installation in a receptacle of a base unit, according to an embodiment of the invention.
Figure 17:
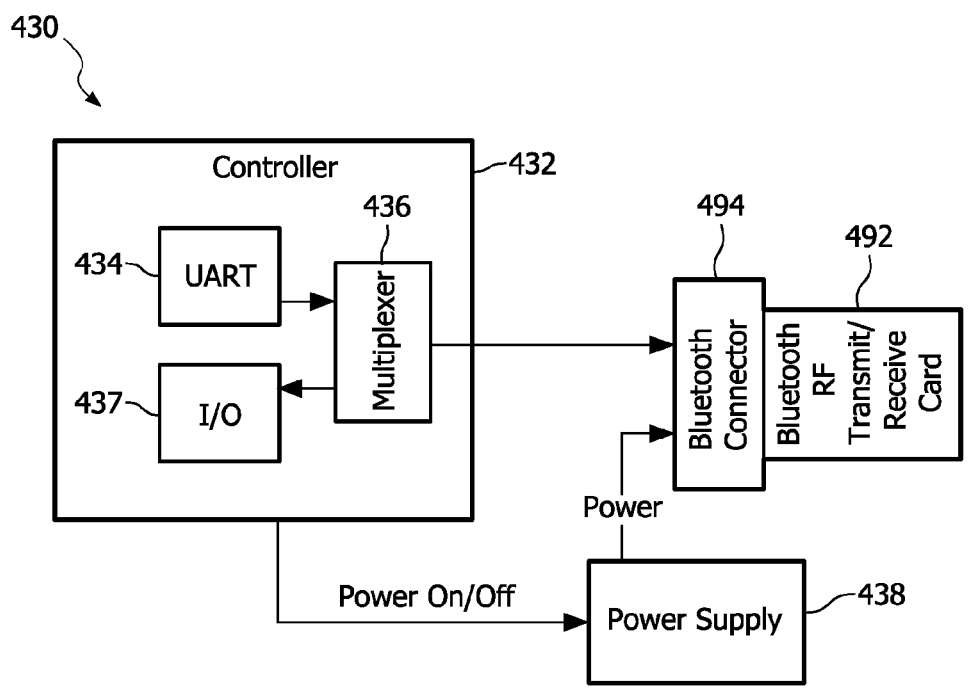
FIG. 17 is a functional block diagram illustrating one embodiment of a modular AED with a communications module.

Another embodiment of the base unit 190 and communication module 192 is shown in FIGS. 15, 16, and 17. FIG. 15 illustrates a modular AED system 300 comprising a base unit 390 and a communications module 392. Base unit 390 and communications module 392 are selectively connected by means of a receptacle 394 located in the battery well of the base unit 390.

FIG. 16 illustrates the advantages arising from disposing receptacle 394 and communications module 392 in the base unit 390 battery well. In addition to the aforedescribed advantages made possible by the invention, this embodiment has an added advantage in that the communications module 392 is protected from breakage and water damage by a battery (not shown) which is installed over the communications module 392. The arrangement also protects the user from touching high voltage that may inadvertently appear across the receptacle contacts during AED operation. Co-assigned U.S. Pat No. 6,108,578, entitled "Configurable Arrhythmia Analysis System" and herein incorporated by reference describes similar safety advantages that are obtained by installing a data card under a battery.

FIG. 17 illustrates one functional block diagram of another embodiment of the invention, in which communications module 392 is a removable RF transceiver 492, which is removably interfaced with a base unit 430 via a connector 494. The RF transceiver 492 is preferably configured as a Bluetooth transceiver, an example of which is manufactured by National Semiconductor Corporation. Power management circuit 438, which may reside within base unit 390, provides power to RF transceiver 492 for operation. Controller 432, comprising UART 434, multiplexer 436, and I/O circuitry 437, controls the flow of data between base unit 430 and RF transceiver 492.

Communication module 192 provides similar functionality and usefulness as the aforedescribed transmitter/receiver 258. Communication module 192 allows communication of data between the AED circuit 230 and a remote location (not shown) such as a hospital via a wireless radio channel. For example, communication module 192 may receive data from the data card 36 via the gate array 234 and transmit the data to the remote location. Or communication module 192 may receive voice data from the microphone 34 or 198 and transmit this data to the remote location. Alternatively, communication module 192 may provide data received from the remote location to the processor 236 via the gate array 234. The processor unit 236 may convert the received data into a voice using the speaker 24.

What is claimed is:

1. A modular defibrillator comprising:
a base unit including a battery located in a battery well of a base unit enclosure, the base unit enclosure containing a power management circuit, a heart rhythm analysis circuit, a shock generating circuit, and a module space located within the battery well for a removable module;
a removable communications module located in the module space of the base unit enclosure; and
a receptacle disposed in the base unit enclosure proximate to the module space which operatively connects the communications module to the base unit.

2. The modular defibrillator of claim 1, wherein the communications module is a radio frequency (RF) transceiver.

3. The modular defibrillator of claim 2, wherein the RF transceiver is a Bluetooth transceiver.

4. The modular defibrillator of claim 1, wherein the receptacle is disposed on a surface of the battery well.

5. The modular defibrillator of claim 4, wherein the battery protectively covers the communications module when the battery is installed in the battery well.

6. The modular defibrillator of claim 1, further comprising a multiplexing circuit.

7. The modular defibrillator of claim 6, wherein the multiplexing circuit is disposed for two-way data communication between the base unit and the communications module.

* * * * *